(12) United States Patent
Misske et al.

(10) Patent No.: US 9,353,043 B2
(45) Date of Patent: May 31, 2016

(54) PREPARATION OF (METH)ACRYLIC ESTERS OF POLYALKOXY-CONTAINING ALCOHOLS

(71) Applicant: BASF SE, Ludwigshafen (DE)

(72) Inventors: Andrea Misske, Speyer (DE); Uwe Meisenburg, Mannheim (DE); Jochen Petzoldt, Weisenheim am Berg (DE); Virginie Bette, Mannheim (DE); Bolette Urtel, Bobenheim-Roxheim (DE); Jean-Marc Ballin, Noisy le Grand (FR)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/620,579

(22) Filed: Feb. 12, 2015

(65) Prior Publication Data

US 2015/0232409 A1 Aug. 20, 2015

Related U.S. Application Data

(60) Provisional application No. 61/940,875, filed on Feb. 18, 2014.

(30) Foreign Application Priority Data

Feb. 18, 2014 (DE) .......................... 10 2014 202 963

(51) Int. Cl.
C07C 67/08 (2006.01)
C08G 65/332 (2006.01)

(52) U.S. Cl.
CPC ............ C07C 67/08 (2013.01); C08G 65/3322 (2013.01)

(58) Field of Classification Search
CPC .......................... C07C 67/08; C08G 65/3322
See application file for complete search history.

(56) References Cited

U.S. PATENT DOCUMENTS

| | | | |
|---|---|---|---|
| 6,040,473 A * | 3/2000 | Knebel et al. | 560/217 |
| 2006/0036063 A1* | 2/2006 | Hofer et al. | 528/367 |
| 2014/0135523 A1 | 5/2014 | Jaeger et al. | |

FOREIGN PATENT DOCUMENTS

| | | |
|---|---|---|
| DE | 196 02 035 A1 | 7/1997 |
| DE | 10 2004 042 799 A1 | 3/2006 |
| DE | 10 2008 040 214 A1 | 1/2010 |
| EP | 0 902 017 A1 | 3/1999 |
| EP | 1 820 812 A1 | 8/2007 |
| FR | 2 739 850 A1 | 4/1997 |
| GB | 1535657 * | 12/1978 |
| JP | 4-66555 A | 3/1992 |
| JP | 2001/097919 * | 4/2001 |
| WO | WO 2014/053347 A1 | 4/2014 |

* cited by examiner

*Primary Examiner* — Shailendra Kumar

(74) *Attorney, Agent, or Firm* — Oblon, McClelland, Maier & Neustadt, L.L.P.

(57) ABSTRACT

In a process for preparing (meth)acrylic esters (E) of polyalkoxy-containing alcohols which comprises reacting polyalkoxy-containing alcohols (P) of formula (I)

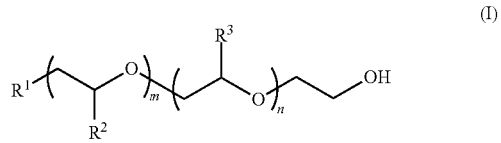

(I)

where $R^1$ is hydrogen, a hydroxyl group or a straight-chain or branched, saturated or unsaturated alcohol of 1 to 30 carbon atoms, $R^2$ and $R^3$ are each independently H or methyl, and m and n are each independently an integer between 0 and 100, with the proviso that m and n cannot both be 0, with a (meth)acrylic anhydride (A) in the presence of at least one basic catalyst (K) having a $pK_B$ value of not more than 7.0 and of at least one sterically hindered polymerization inhibitor, the reaction mixture is quenched with a $C_1$-$C_6$ alkanol after the reaction has ended.

19 Claims, No Drawings

PREPARATION OF (METH)ACRYLIC ESTERS OF POLYALKOXY-CONTAINING ALCOHOLS

This application claims benefit of 61/940,875, filed on Feb. 18, 2014.

The present invention relates to a process for catalytically preparing (meth)acrylic esters of polyalkoxy-containing alcohols by reacting these alcohols with a (meth)acrylic anhydride.

The terms (meth)acrylic acid, (meth)acrylic ester and (meth)acrylic anhydride are to be understood in the context of the present invention as meaning, respectively, acrylic acid and/or methacrylic acid, acrylic ester and/or methacrylic ester, which are herein also referred to as (meth)acrylates, and acrylic anhydride and/or methacrylic anhydride.

(Meth)acrylic esters are usually prepared by catalytic esterification of (meth)acrylic acid or transesterification of other (meth)acrylic esters with alcohols. Strong acids or bases are frequently used in the reaction, so acid- or base-sensitive (meth)acrylic esters are typically not intentionally obtainable in this way by esterification or transesterification.

(Meth)acrylic esters of polyalkoxy-containing alcohols are known. The literature comprises several documents describing the transesterification of polyalkoxy-containing alcohols with a (meth)acrylic ester, for instance EP 0 902 017 A1, JP 04 066555 A1 and DE 196 02 035 A1.

A potential alternative to esterification/transesterification is reacting an alcohol with a (meth)acrylic anhydride.

FR 2 739 850 discloses a process for preparing (meth)acrylates of R-substituted polyalkoxy-containing alcohols having 3 to 60 EO and PO units by reaction with (meth)acrylic anhydride. The substituent R may be alkyl, aryl, alkylaryl or further substituted. Catalysts disclosed are Brönstedt acids (sulfuric acid, alkyl- or arylsulfonic acids), Lewis acids ($BF_3$) and amines (methylimidazole, diethylamine, triethylamine) in a concentration of 0.1 to 5 wt %.

European application EP 1 820 812 A1 describes a process for preparing polyether (alkyl)acrylates by reacting polyether alcohols with an (alkyl)acrylate in the presence of liganded main group 3 or 4 and transition groups 3-8 metal catalysts.

DE 10 2008 040 214 A1 discloses the preparation of poylalkylene glycol di(meth)acrylates by reaction of polyalkylene glycol with (meth)acrylic anhydride. The reaction is carried out without a catalyst. The recommended polymerization inhibitors are the customary stabilizers such as phenothiazine, hydroquinone monomethyl ether but also sterically hindered phenols such as 2,4-dimethyl-6-tert-butylphenol.

German laid-open application DE 10 2004 042 799 A1 likewise discloses a process for preparing poly($C_2$-$C_4$ alkylene glycol) mono(meth)acrylic esters. The reaction of an alcohol with a (meth)acrylic anhydride is again carried out in the presence of sterically hindered polymerization inhibitors by use of basic catalysts such as sparingly soluble mono- or divalent metal oxides, hydroxides, carbonates and bicarbonates. According to the disclosure, the water content of the reaction batch is less than 0.2%, preferably less than 1000 ppm. It is recommended that in the event of water contents being higher, the water is first removed before the anhydride is added.

The processes disclosed in the prior art are disadvantageous in that water is included in the reaction batch to hydrolyze unconverted (meth)acrylic anhydride. Yet this water has to be removed again if the presence of water is undesirable for the later use of the (meth)acrylic esters of polyalkoxy-containing alcohols, for example in certain polymerization processes.

The problem addressed by the present invention was that of providing an alternative process for preparing (meth)acrylic esters of polyalkoxy-containing alcohols in high purity to obtain in particular (meth)acrylic esters of this type which are water free, have a low residual alcohol content and contain but minimal amounts of catalyst residues.

The problem was solved by a process for preparing (meth)acrylic esters (E) of polyalkoxy-containing alcohols, which comprises reacting polyalkoxy-containing alcohols (P) of formula (I)

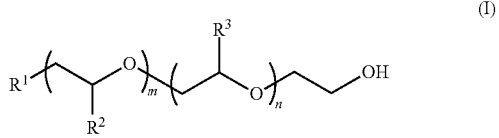

where
$R^1$ is hydrogen, a hydroxyl group or a straight-chain or branched, saturated or unsaturated alcohol of 1 to 30 carbon atoms,
$R^2$ and $R^3$ are each independently H or methyl, and
m and n are each independently an integer between 0 and 100, with the proviso that m and n cannot both be 0,
with a (meth)acrylic anhydride (A) in the presence of at least one basic catalyst (K) having a $pK_B$ value of not more than 7.0 and of at least one sterically hindered polymerization inhibitor, wherein the reaction mixture is quenched with a $C_1$-$C_6$ alkanol after the reaction has ended.

The process of the present invention provides (meth)acrylic esters (E) of polyalkoxy-containing alcohols with high conversions for the polyalkoxy-containing alcohol (P). The end product further has a low alkali content and a low (meth)acrylic acid content. What is particularly important is that the end product is almost water free.

Water free is to be understood in the context of the present invention as meaning that the water content is below 5 wt %, preferably less than 2 wt % and more preferably less than 1 wt %, all based on the end product.

In the polyalkoxy-containing alcohols typically used as polyalkoxy-containing alcohols (P), $R^2$ and $R^3$ are each independently hydrogen or methyl, so an ethylene oxide or propylene oxide unit is concerned, more preferably an ethylene oxide unit.

It will be appreciated that the polyalkoxy-containing alcohol used may comprise two or more different alkylene oxide units, in which case the alkylene oxide units may form a random distribution, but they may also form a blocked arrangement. However, the polyalkoxy-containing alcohols (P) may also only comprise one group of alkylene oxide units, preferably ethylene oxide units.

The numbers m and n of alkylene oxide units in the polyalkoxy-containing alcohol (P) are each typically between 1 and 100 independently of each other, so in the case of m=1 and n=0 or m=0 and n=1 a monoalkoxyalcohol is thus concerned. m and n are each preferably in the range between 5 and 90, more preferably between 5 and 50 and yet more preferably between 10 and 50 independently of each other.

The substituent $R^1$ is hydrogen, a hydroxyl group or a straight-chain or branched, saturated or unsaturated alcohol of 1 to 30 carbon atoms. Examples thereof are monoalcohols of 1 to 12 carbon atoms, e.g. methanol, ethanol, isopropanol, n-propanol, n-butanol, isobutanol, sec-butanol, tert-butanol, n-hexanol, n-heptanol, n-octanol, n-decanol, 2-ethylhexanol.

Preferably, however, the substituent $R^1$ comprises straight-chain, saturated or unsaturated primary alcohols of 6 to 22 carbon atoms, known as fatty alcohols. Fatty alcohols of this type include, for example, hexan-1-ol (hexyl alcohol, caproic alcohol), heptan-1-ol (heptyl alcohol, enanthic alcohol), octan-1-ol (octyl alcohol, capryl alcohol), nonan-1-ol (nonyl alcohol, pelargonyl alcohol), decan-1-ol (decyl alcohol, capric alcohol), undecan-1-ol (undecyl alcohol), undec-10-en-1-ol, dodecan-1-ol (dodecyl alcohol, lauryl alcohol), tridecan-1-ol (tridecyl alcohol), tetradecan-1-ol (tetradecyl alcohol, myristyl alcohol), pentadecan-1-ol (pentadecyl alcohol), hexadecan-1-ol (hexadecyl alcohol, cetyl alcohol, palmityl alcohol), heptadecan-1-ol, heptadecyl alcohol), octadecan-1-ol (octadecyl alcohol, stearyl alcohol), 9-cis-octadecen-1-ol (oleyl alcohol), 9-trans-octadecen-1-ol (elaidyl alcohol), nonadecan-1-ol (nonadecyl alcohol), eicosan-1-01 (eicosyl alcohol, arachyl alcohol), 9-cis-eicosen-1-ol (gadoleyl alcohol), heneicosan-1-ol (heneicosyl alcohol), docosan-1-ol (docosyl alcohol, behenyl alcohol), 13-cis-docosen-1-ol (erucyl alcohol), 13-trans-docosen-1-ol (brassidyl alcohol). It will be appreciated that isomer mixtures of these alcohols can also be used.

It is further also possible to use comparatively high molecular weight alcohols such as lignoceryl alcohol ($C_{24}H_{50}O$), ceryl alcohol ($C_{26}H_{54}O$) or myricyl alcohol ($C_{30}H_{62}O$) as substituent $R^1$.

Preferably, however, the aforementioned fatty alcohols of 6 to 22 carbon atoms are used. It is preferable to use fatty alcohols of 8 to 18, preferably of 10 to 16 carbon atoms. Any desired mixtures of fatty alcohols may be concerned, for example a mixture of fatty alcohols having a $C_{16}$ and a $C_{18}$ alkyl chain, having a $C_{13}$ and a $C_{15}$ alkyl chain or having a $C_{12}$ and a $C_{14}$ alkyl chain. Preferred mixtures of fatty alcohols are those having a $C_{16}$ and a $C_{18}$ alkyl chain.

The polyalkoxy-containing alcohols useful in the process of the present invention are available from BASF SE under the Lutensol® or Pluriol® brand names for example.

The reaction step comprises reaction with a (meth)acrylic anhydride (A) in the presence of at least one basic catalyst (K) having a $pK_B$ value of not more than 7.0.

Basic catalysts having a $pK_B$ value of not more than 7.0, preferably of not more than 5.0 and more preferably of not more than 3.0 are suitable.

All bases such as alkali metal and alkaline earth metal hydroxides and also inorganic salts are suitable in principle. Alkali metal and alkaline earth metal hydroxides may be used not only in solid form but also as solutions in solvents, for example as aqueous solutions. Inorganic salts useful in the present invention are preferably inorganic salts.

Useful alkali metal and alkaline earth metal hydroxides include particularly lithium hydroxide, sodium hydroxide, potassium hydroxide, magnesium hydroxide and calcium hydroxide. Aqueous solutions of sodium hydroxide, potassium hydroxide and calcium hydroxide and/or mixtures or suspensions with sodium hydroxide, potassium hydroxide and calcium hydroxide can also be used. Such aqueous solutions/mixtures/suspensions comprise 10 to 90 wt % of water, preferably 20 to 80 wt % of water and more preferably 40 to 60 wt % of water.

The inorganic salt preferably includes at least one anion selected from the group consisting of carbonate ($CO_3^{2-}$), bicarbonate ($HCO_3^-$), phosphate ($PO_4^{3-}$), hydrogenphosphate ($HPO_4^{2-}$), dihydrogenphosphate ($H_2PO_4^-$), sulfate ($SO_4^{2-}$), sulfite ($SO_3^{2-}$) and carboxylate ($R^4$—COO—), where $R^4$ is $C_1$-$C_{18}$ alkyl; $C_2$-$C_{18}$ alkyl optionally interrupted by one or more oxygen and/or sulfur atoms and/or one or more substituted or unsubstituted imino groups; or $C_6$-$C_{14}$ aryl.

The collective terms for $R^4$ specified in the case of carboxylate ($R^1$—COO—) are each defined as follows:

$C_1$-$C_{18}$ alkyl: straight-chain or branched hydrocarbon radicals having up to 18 carbon atoms, preferably $C_1$-$C_{10}$ alkyl such as methyl, ethyl, propyl, isopropyl, n-butyl, sec-butyl, tert-butyl, 1,1-dimethylethyl, pentyl, 2-methylbutyl, 1,1-dimethylpropyl, 1,2-dimethylpropyl, 2,2-dimethylpropyl, 1-ethylpropyl, hexyl, 2-methylpentyl, 3-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, 2,4,4-trimethylpentyl, 1,1,3,3-tetramethylbutyl, nonyl and decyl, and isomers thereof.

$C_6$-$C_{14}$ aryl: a mono- to tricyclic aromatic ring system comprising 6 to 14 carbon ring members, for example phenyl, naphthyl and anthracenyl, preferably a mono- to bicyclic, more preferably a monocyclic, aromatic ring system.

Preferred anions are carbonate, bicarbonate, phosphate, hydrogenphosphate, sulfate, sulfite and carboxylate, while carbonate and phosphate are particularly preferred.

Phosphate also comprehends the condensation products, for example diphosphates, triphosphates and polyphosphates.

The inorganic salt preferably includes at least one and more preferably exactly one cation selected from the group consisting of alkali metals, alkaline earth metals, ammonium, cerium, iron, manganese, chromium, molybdenum, cobalt, nickel and zinc.

Alkali metals are preferred and lithium, sodium and potassium are particularly preferred.

Particularly preferred inorganic salts are $Li_3PO_4$, $K_3PO_4$, $Na_3PO_4$, $K_2CO_3$ and $Na_2CO_3$ and also hydrates thereof, while $Na_2CO_3$ and $K_3PO_4$ are very particularly preferred.

The inorganic salt may be added as a solid material, i.e., as the pure substance, or as a solution in a suitable solvent. It is preferable to add the salt as a solid material and not to admix to the reaction system any further component which has to be removed in a costly and/or inconvenient manner.

According to the present invention, the polyalkoxy-containing alcohols (P) are reacted with at least one mole equivalent of acrylic anhydride or methacrylic anhydride or a mixture thereof. (Meth)acrylic anhydride here and hereinafter denotes not only acrylic anhydride or methacrylic anhydride but also mixtures thereof.

(Meth)acrylic anhydride can also be used in a small excess which, however, will not exceed 35 mol %, preferably 25 mol %, especially 15 mol % and advantageously 10 mol %, based on 1 mol of polyalkoxy-containing alcohol (P), i.e., the amount of (meth)acrylic anhydride in the present invention is not more than 1.35 mol, preferably not more than 1.25 mol, especially not more than 1.20 mol and advantageously not more than 1.15 mol per mole of polyalkoxy-containing alcohol (P). Preferably at least 1.005 mol, especially at least 1.01 mol and more preferably at least 1.02 mol of (meth)acrylic anhydride are used per mole of polyalkoxy-containing alcohol (P).

Temperatures at which the anhydride is reacted with the polyalkoxy-containing alcohol (P) are preferably in the range from 0 to 150° C., especially in the range from 20 to 130° C. and more preferably in the range from 50 to 100° C. The prevailing pressure during the reaction is of minor importance for the success of the reaction and is typically in the range from 800 mbar to 2 bar and frequently equal to ambient pressure. The reaction of the anhydride with the polyalkoxy-containing alcohol (P) can be carried out in any apparatus customary for reactions of this type, for example in a stirred tank, in stirred tank batteries, autoclaves, tubular reactors or kneaders.

The reaction of the anhydride with the polyalkoxy-containing alcohol (P) is preferably carried on to a conversion of at least 80%, especially at least 90% and more preferably at least 95% for feed alcohol (P). The reaction times required for this will typically not exceed 6 h and frequently amount to about 4 h. The reaction can be tracked via $^1$H NMR spectroscopy of the reaction mixture, preferably via derivatization with trichloroacetyl isocyanate (TAI).

The reaction of the anhydride with the polyalkoxy-containing alcohol (P) can be carried out without addition of solvents, or in inert solvents or diluents. Inert solvents are typically aprotic compounds. Inert solvents include optionally halogenated aromatic hydrocarbons such as toluene, o-xylene, p-xylene, cummene, chlorobenzene, ethylbenzene, technical-grade mixtures of alkyl aromatics, aliphatic and also cycloaliphatic hydrocarbons such as hexane, heptane, octane, isooctane, cyclohexane, cycloheptane, technical-grade aliphatics mixtures, further ketones such as acetone, methyl ethyl ketone, cyclohexanone, further ethers such as tetrahydrofuran, dioxane, diethyl ether, tert-butyl methyl ether, and also mixtures of the aforementioned solvents, e.g., toluene/hexane. It is preferable to use very little if any solvent, typically less than 10 wt %, based on the feed materials, i.e., to perform the reaction in substance.

The process of the present invention is notable in particular because the reaction of the anhydride with the polyalkoxy-containing alcohol (P) can also be carried out in the presence of considerable amounts of water. This is advantageous in relation to the prior art (e.g., DE 10 2004 042 799 A1), where the water is removed, for example by distillation, prior to the reaction. There is no need for this in the process of the present invention, so the reaction mixture may perfectly well comprise up to 50 mol %, preferably up to 25 mol % and more preferably up to 10 mol % of water (based on the alcohol used). The term "reaction mixture" refers to the mixture of reactants A and P with the base and also with inhibitor and any solvent used. The alcohol used, i.e., compound P, may customarily comprise water, for example up to 0.5 wt %, based on total alcohol.

The reaction will customarily be carried out by making the reaction mixture comprising the polyalkoxy-containing alcohol (P), the anhydride and the base, the inhibitor and any solvent react at the temperatures specified above. It is preferable to charge the alcohol (P), the inhibitor and the base and also any solvent initially and to add the anhydride thereto. The anhydride is preferably added at reaction temperature. It is very particularly preferable to add some of the anhydride before the base, some thereafter.

It has also been found to be advantageous to perform the reaction of the anhydride with the polyalkoxy-containing alcohol (P) in the presence of a polymerization inhibitor to avoid any uncontrolled polymerization. The process of the present invention utilizes sterically hindered polymerization inhibitors, for example sterically hindered phenols such as 2,6-di-tert-butylphenol or 2,6-di-tert-butyl-4-methylphenol (butylhydroxytoluene, BHT) and thioazines such as phenothiazine. The sterically hindered polymerization inhibitors used preferably do not degrade during the course of the reaction like, for example, the hydroquinones (hydroquinone, methylhydroquinone) customarily used as polymerization inhibitors. 2,6-Di-tert-butyl-4-methylphenol (butylhydroxytoluene, BHT) is a particularly preferred sterically hindered polymerization inhibitor.

Polymerization inhibitors can still further be added to the reaction mixture in addition to the aforementioned sterically hindered polymerization inhibitors. Suitable are the polymerization inhibitors known for reactions of this type, in particular hydroquinone, hydroquinone monomethyl ether (MEHQ), 2,4-dimethyl-6-tert-butylphenol (Topanol A), methylene blue, cerium(III) salts such as cerium(III) acetate, and also nitroxides, in particular sterically hindered nitroxides, i.e., nitroxides of secondary amines where the carbon atoms adjacent to the nitroxide group each bear 3 alkyl groups such that 2 at a time of these alkyl groups, in particular those not positioned on the same carbon atom, combine with the nitrogen atom of the nitroxide group and with the carbon atom to which they are attached to form a saturated 5- or 6-membered ring, for example in 2,2,6,6-tetramethyl-1-piperidinyloxy (TEMPO) or 4-hydroxy-2,2,6,6-tetramethyl-1-piperidinyloxy (OH TEMPO), mixtures of the aforementioned inhibitors, mixtures of the aforementioned inhibitors with oxygen, for example in the form of air, or mixtures of mixtures of the aforementioned inhibitors with oxygen, for example in the form of air. Preferred polymerization inhibitors from this group are hydroquinone monomethyl ether (MEHQ) and 2,4-dimethyl-6-tert-butylphenol (Topanol A).

The amount of inhibitor may be up to 2 wt %, based on the overall amount of anhydride and polyalkoxy-containing alcohol (P). Inhibitors are advantageously used in amounts of 10 ppm to 1000 ppm, based on the overall amount of anhydride and polyalkoxy-containing alcohol (P). In the case of inhibitor mixtures, these particulars relate to total components other than oxygen.

The reaction of polyalkoxy-containing alcohol (P) with (meth)acrylic anhydride leads naturally primarily to a mixture of (meth)acrylic ester of polyalkoxy-containing alcohol (P) with acrylic acid or methacrylic acid with or without residues of excess anhydride and unconverted polyalkoxy-containing alcohol (P).

However, excess anhydride typically comprises not more than 10 wt % and particularly not more than 5 wt % of the originally used amount of (meth)acrylic anhydride A.

It is accordingly an essential feature of the present invention that excess anhydride is removed by a quench with a $C_1$-$C_6$ alkanol, such as methanol, ethanol, propanol, butanol, pentanol and hexanol, and also isomers thereof such as isopropanol, isobutanol, tert-butanol and the isomers of pentanol and hexanol. Preferred $C_1$-$C_6$ alkanols are methanol, ethanol, propanol and n-butanol, while methanol and ethanol are particularly preferred. It will be appreciated that mixtures of the recited $C_1$-$C_6$ alkanols can also be used, but preferably only one of the recited $C_1$-$C_6$ alkanols is used.

The customary procedure is for a reaction time of up to 6 h to be followed by cooling down and the addition of the $C_1$-$C_6$ alkanol. The mixture is subsequently further stirred for up to 2 h, preferably up to 1 h, but not less than 30 minutes. If desired, excess $C_1$-$C_6$ alkanol may subsequently be removed again by customary methods of separation, for example by distillation.

The amounts in which the $C_1$-$C_6$ alkanol is added to the reaction medium range up to 5 wt %, preferably up to 3 wt %, more preferably up to 2 wt % and especially up to 1 wt %, all based on total reaction medium. However, the amount of $C_1$-$C_6$ alkanol added for quenching is not less than 0.5 wt %, based on total reaction medium.

The polyalkoxy-containing alcohol (meth)acrylate esters (E) obtained according to the present invention are useful, for example, as monomers or comonomers in the production of dispersions, for example acrylic dispersions, as reactive diluents, for example in radiation-curable coating compositions or in paints, preferably in exterior paints, and also in dispersions for use in the paper sector, in the cosmetic sector, in the pharma sector, in agroformulations, in the textile industry and in the oil production sector.

The examples which follow are offered by way of elucidation, not limitation, of the properties of the invention.

EXAMPLES

Unless otherwise stated, "parts" and "%" herein are "parts by weight" and "wt %", respectively.

TAI NMR was used as analytical method to detect the low concentrations of residual alcohol. In this method, the residual alcohol is quantitatively derivatized with trichloroacetyl isocyanate (TAI), and the integrals of the ester signals may be compared. Stabilizer concentrations in the samples were determined with HPLC.

Example 1

Preparation of Lutensol® AT25 Methacrylate Ester Using Sodium Carbonate as Catalyst To a 750 mL flange flask fitted with an anchor stirrer (250 rpm) and a condenser were added 403 g (0.3 mol) of a pulverulent polyethoxyalcohol (Lutensol® AT25 from BASF SE, ethoxylation degree about 25, $M_w$ about 1360 g/mol, contained about 0.5 wt % of water) as initial charge and melted at a bath temperature of 75-100° C. While maintaining a pot temperature of 70° C. and passing air through the flask at a rate of 3.5 L/h, 184 mg (400 ppm) of butylhydroxytoluene (BHT, 2,6-di-tert-butyl-4-methylphenol) as stabilizer, 56.6 g (0.345 mol, 94 wt % strength) of methacrylic anhydride comprising 2000 ppm (113 mg) of 2,4-dimethyl-6-tert-butylphenol (Topanol A), and also 478 mg (1.5 mol %) of sodium carbonate were added and stirred in. The pot temperature was raised to 90-95° C. After 6 hours, the pot temperature was cooled down to 60° C. and 4.6 g (0.14 mol) of methanol were added. After a further hour, the mixture was removed while still warm, for analysis.

Analysis (TAI NMR) shows the following composition: 93.8% Lutensol® AT25 methacrylate ester and 6.2% methacrylic acid. Residual alcohol, methacrylic anhydride and methanol could not be detected in the sample.

Stabilizer concentrations as determined via HPLC were: 360 ppm of BHT and <100 ppm of Topanol A.

Comparative Examples 1a-1f

Preparation of Lutensol® AT25 Methacrylate Ester Using Acidic Catalysts with or without Quenching with Water The reaction was carried out similarly to Example 1 under the following conditions: pot temperature 90-95° C., molar alcohol:anhydride ratio 1:1.33. The alcohol used contained 22 mol % of water. Different catalysts were used as well as none. Another effect investigated was that of a hydrolysis with water, by using 27 mol % of water. The reaction time was extended by 1 hour for a hydrolysis. The results are summarized in table 1.

To make it easier to compare the values, the methacrylic acid released was left out of the calculations.

TABLE 1

| Comparative Example | Catalyst/ quench with $H_2O$ | t [h] | Conversion [%] | Product [%] | Residual alcohol [%] | Anhydride [%] |
|---|---|---|---|---|---|---|
| 1a | none/no | 6 | 96 | 95.4 | 3.6 | 1.1 |
| 1b | none/yes | 6 + 1 | 98 | 96.5 | 1.9 | 1.7 |
| 1c | $Ph_3P$/no | 6 | 98 | 96.4 | 2.0 | 1.7 |
| 1d | $Ph_3P$/yes | 6 + 1 | 98 | 96.8 | 1.7 | 1.5 |
| 1e | methanesulfonic acid/no | 6 | 96 | 94.8 | 3.6 | 1.6 |
| 1f | methanesulfonic acid/yes | 6 + 1 | 98 | 96.8 | 1.7 | 1.5 |

It is clear from Comparative Examples 1a to 1f that conversion is incomplete without catalyst. The use of catalysts such as $Ph_3P$ and methanesulfonic acid likewise led to incomplete conversion. Neither the quench with water nor the water in the alcohol caused the anhydride to hydrolyze.

Examples 2a-2c

Preparation of Lutensol® AT25 Methacrylate Ester Using Basic Catalysts at Low Concentration The reaction was carried out similarly to Example 1. The reference used was a reaction procedure with subsequent quench with water. In all examples, pot temperature was 90-94° C., and the molar alcohol:anhydride ratio was 1:1.1. A pot temperature of 100° C. was used for the quench with water in the reference test, and of 62-63° C. for the quench with methanol. The alcohol used contained 0.5 wt % of water. The reaction conditions and results are summarized in tables 3a and 3b. The methacrylic acid formed was left out of the calculations to make the values easier to compare.

TABLE a

| | Reaction conditions | | | |
|---|---|---|---|---|
| Example | Catalyst | Reaction time [h] | Quench | Quench time [h] |
| reference | $K_3PO_4$ (1 mol %) | 7 | 2.5 wt % $H_2O$ | 2 |
| 2a | $Na_2CO_3$ (1 mol %) | 6 | 5 wt % methanol | 1 |
| 2b | $Na_2CO_3$ (1.5 mol %) | 6 | 3 wt % methanol | 0.5 |
| 2c | $Na_2CO_3$ (1.5 mol %) | 6 | 3 wt % methanol | 1 |

TABLE 2b

| | Results | | |
|---|---|---|---|
| Example | Product [%] | Residual alcohol [%] | Anhydride [%] |
| reference | 95.8 | 4 | 0.2 |
| 2a | 97.6 | 2.4 | 0 |
| 2b | 98.0 | 2 | 0 |
| 2c | 97.1 | 3 | 0 |

Example 3

Preparation of Lutensol® AT25 Methacrylate Ester Using Basic Catalysts at Low Concentration The reaction was carried out similarly to Example 1. The reference used was a reaction procedure without quench.

Both examples were carried out with a pot temperature of 90-93° C. and a molar alcohol:anhydride ratio of 1:1.05. The catalyst used was $K_3PO_4$ (1 mol %). The reaction time was 4 hours in both cases. The quench with ethanol took place at a pot temperature of 78° C. and the quench time was 2 hours. The alcohol used contained 0.5 wt % of water. Reaction conditions and results are summarized in table 4. The methacrylic acid formed was left out of the calculations to make the values easier to compare.

TABLE 3

| Example | Product [%] | Residual alcohol [%] | Anhydride [%] |
|---|---|---|---|
| reference | 93.8 | 5.7 | 0.5 |
| 3 | 89.0 | 4.4 | 0 |

Despite the 5.7 wt % residual alcohol content still remaining in the reference test, anhydride is still present, but it is fully converted by the addition of ethanol. The product of Example 3 still contained an additional 6.6% of ethanol.

Example 4

Preparation of Lutensol® AT25 Methacrylate Ester Using Sodium Carbonate as Catalyst To a 4 L flange flask fitted with an inclined blade stirrer (350 rpm), baffles and a condenser were added 2016 g (1.5 mol) of a pulverulent polyethoxy alcohol (Lutensol® AT25 from BASF SE, ethoxylation degree about 25, $M_w$ about 1360 g/mol, contained about 0.5 wt % of water) as initial charge and melted at a bath temperature of 75-100° C. While maintaining a pot temperature of 61° C. and passing air through the flask at a rate of 3.5 L/h, 919 mg (400 ppm) of butylhydroxytoluene (BHT, 2,6-di-tert-butyl-4-methylphenol) as stabilizer, 283 g (1.725 mol, 94 wt % strength) of methacrylic anhydride comprising 2000 ppm (566 mg) of 2,4-dimethyl-6-tert-butylphenol (Topanol A), and also 2.39 mg (1.5 mol %) of sodium carbonate were added and stirred in. The pot temperature was raised to 90-95° C. After 6 hours, the pot temperature was cooled down to 60° C. and 23 g (0.72 mol) of methanol were added. After a further hour, the mixture was admixed with pure methacrylic acid (stabilized with 200 ppm of MEHQ) and adjusted to a methacrylic acid content of 50 wt % and removed for analysis.

Analysis (TAI NMR) showed the composition summarized in table 4 versus the course of the reaction:

TABLE 4

| Sample | Product [%] | Residual alcohol [%] | Anhydride [%] | Methacrylic acid [%] |
|---|---|---|---|---|
| after 4 h | 93.0 | 0 | 0.7 | 6.3 |
| after 6 h | 93.2 | 0 | 0.1 | 6.7 |
| after 1 h quench | 93.4 | 0 | 0 | 6.6 |
| after dilution with methacrylic acid | 49.6 | 0.1 | 0 | 50.3 |

The course of the reaction shows that the concentration of anhydride in the reaction mixture was down to just 0.7 wt % after 4 hours and down to just 0.1 wt % after 6 hours. After the quench with methanol, anhydride conversion is complete.

Example 5

Preparation of Lutensol® AT25 Methacrylate Ester Using Aqueous Sodium Hydroxide Solution as Catalyst To a 750 mL flange flask fitted with an inclined blade stirrer (350 rpm), baffles and a condenser were added 403 g (0.3 mol) of a pulverulent polyethoxy alcohol (Lutensol® AT25 from BASF SE, ethoxylation degree about 25, $M_w$ about 1360 g/mol, contained about 0.5 wt % of water) as initial charge and melted at a bath temperature of 75-100° C. While maintaining a pot temperature of 68° C. and passing air through the flask at a rate of 3.5 L/h, 184 mg (400 ppm) of butylhydroxytoluene (BHT, 2,6-di-tert-butyl-4-methylphenol) as stabilizer, 56.6 g (0.345 mol, 94 wt % strength) of methacrylic anhydride comprising 2000 ppm (113 mg) of 2,4-dimethyl-6-tert-butylphenol (Topanol A), and also 50 wt % (0.36 g, 1.5 mol %) aqueous sodium hydroxide solution were added and stirred in. The pot temperature was raised to 90-95° C. After 6 hours, the pot temperature was cooled down to 60° C. and 4.6 g (0.14 mol) of methanol were added. After a further hour, the mixture was removed while still warm, for analysis.

Analysis (TAI NMR) showed the composition summarized in table 6 versus the course of the reaction:

TABLE 5

| Sample | Product [%] | Residual alcohol [%] | Anhydride [%] | Methacrylic acid [%] |
|---|---|---|---|---|
| after 4 h | 92.4 | 1.1 | 0.5 | 6.0 |
| after 6 h | 93.6 | 0 | 0.4 | 5.9 |
| after 1 h quench | 94.5 | 0 | 0 | 5.4 |

The use of aqueous sodium hydroxide solution as catalyst surprisingly shows that it did not cause the anhydride to hydrolyze but nonetheless led to complete conversion of the alcohol.

Example 6

Preparation of Lutensol® AT25 Methacrylate Ester Using Later Addition of Aqueous Sodium Hydroxide Solution as Catalyst To a 750 mL flange flask fitted with an inclined blade stirrer (500 rpm), baffles and a condenser were added 605 g (0.45 mol) of a pulverulent polyethoxy alcohol (Lutensol® AT25 from BASF SE, ethoxylation degree about 25, $M_w$ about 1360 g/mol, contained about 0.15 wt % of water) as initial charge and melted at a bath temperature of 75-100° C. While maintaining a pot temperature of 76° C. and passing air through the flask at a rate of 3.5 L/h, 276 mg (400 ppm) of butylhydroxytoluene (BHT, 2,6-di-tert-butyl-4-methylphenol) as stabilizer, 66.5 g (0.405 mol, 94 wt % strength) of methacrylic anhydride comprising 2000 ppm of 2,4-dimethyl-6-tert-butylphenol (Topanol A) were added and stirred in. The pot temperature was raised to 90-95° C. After 30 minutes, a further 14.8 g (0.09 mol) of methacrylic anhydride and also 50 wt % (0.72 g, 2 mol %) aqueous sodium hydroxide solution were metered in. After 6 hours, the pot temperature was cooled down to 55° C. and 10.4 g (0.32 mol) of methanol were added. After a further hour, the mixture was removed while still warm, for analysis.

Analysis (TAI NMR) showed the composition summarized in table 7 versus the course of the reaction:

TABLE 6

| Sample | Product [%] | Residual alcohol [%] | Anhydride [%] | Methacrylic acid [%] | Methanol [%] |
|---|---|---|---|---|---|
| after 4.5 h | 92.6 | 1.0 | 0.5 | 6.0 | 0 |
| after 6 h | 93.5 | 0 | 0.4 | 6.0 | 0 |
| after 1 h quench | 93.7 | 0 | 0 | 5.9 | 0.4 |

Example 7

Preparation of Lutensol® AT25 Methacrylate Ester, Influence of Polymerization Inhibitors To a 750 mL flange flask fitted with an anchor stirrer (350 rpm) and a condenser were added 252.6 g (0.19 mol) of a pulverulent polyethoxyalcohol (Lutensol® AT25 from BASF SE, ethoxylation degree about 25, $M_w$ about 1360 g/mol, contained about 0.15 wt % of water) as initial charge and melted at a bath temperature of 75-100° C. While air was passed through the flask at a rate of 3.5 L/h, 210 mg (730 ppm) of methylhydroquinone monomethyl ether (MEHQ) as stabilizer and 34.8 g (0.21 mol, 94 wt % strength) of methacrylic anhydride containing 2000 ppm of 2,4-dimethyl-6-tert-butylphenol (Topanol A) were added and stirred in. The pot temperature was raised to 90-95° C. After the reaction had ended, the reaction mixture was cooled down to room temperature and the polymerization onset temperature was determined. The reaction mixture polymerized on remelting at a bath temperature of 85° C.

Similar tests were carried out with MEHQ and BHT as stabilizer, the results are summarized in table 7.

TABLE 7

| Example | Topanol A [ppm] | Stabilizer [ppm] | Reaction start T-onset [C.] | Reaction end T-onset [° C.] |
|---|---|---|---|---|
| 7a | 240 | MEHQ (730) | 119 | — (polymerization) |
| 7b | 235 | BHT (200) | 134 | 128 |
| 7c | 235 | BHT (400) | 144 | 144 |

Investigation of the polymerization onset revealed that they changed during the reaction when MEHQ is used. When, however, a sterically hindered polymerization inhibitor such as BHT is used, the onset remains stable. The reaction mixtures were remeltable without polymerizing.

Example 8

Reaction of Lutensol® AT 11 with Methacrylic Anhydride and Sodium Carbonate as Catalyst To a 1.6 L flange flask fitted with an anchor stirrer and baffles (220 rpm) and also a condenser were added 1018 g of Lutensol® AT 11 (1.4 mol) as initial charge and melted at 75-100° C. bath temperature. While maintaining a pot temperature of 74° C., 507 mg of BHT (400 ppm), 248 g of methacrylic anhydride (1.6 mol, 94% strength, containing 2000 ppm of Topanol A) and also $Na_2CO_3$ (2.07 g, 1.5 mol %) were added while passing air through the flask at 3.5 L/h. The pot temperature was raised to 90-95° C.

After 6 h, the mixture was cooled down to 75° C. pot temperature and admixed with methanol (38 g, 2 wt %). After 1 h, the mixture was adjusted with methacrylic acid (MAA, pure, stabilized with 200 ppm of MEHQ) to a methacrylic acid content of 40% and cooled down.

The samples (TAI-NMR) show the following composition:

| Sample | Lutensol ® AT 11 [wt %] | Anhydride [wt %] | Ester [wt %] | MAA [wt %] |
|---|---|---|---|---|
| after 6 h | 0 | 0.7 | 87.7 | 11.6 |
| after 1 h | 0 | 0 | 87.4 | 12.6 |
| after dilution with MAA | 0 | 0 | 40.2 | 59.8 |

Example 9

Reaction of Lutensol® AT 50 with Methacrylic Anhydride and Sodium Carbonate as Catalyst To a 1.6 L flange flask fitted with an anchor stirrer and baffles (220 rpm) and also a condenser were added 1125 g of Lutensol® AT 11 (0.46 mol) as initial charge and melted at 75-100° C. bath temperature. While maintaining a pot temperature of 65° C., 484 mg of BHT (400 ppm), 86.4 g of methacrylic anhydride (0.53 mol, 94% strength, containing 2000 ppm of Topanol A) and also $Na_2CO_3$ (0.73 g, 1.5 mol %) were added while passing air through the flask at 3.5 L/h. The pot temperature was raised to 90-95° C.

After 6 h, the mixture was cooled down to 66° C. pot temperature and admixed with methanol (36 g). After 1 h, the mixture was adjusted with methacrylic acid (MAA, pure, stabilized with 200 ppm of MEHQ) to a methacrylic acid content of 45% and cooled down.

The samples (TAI-NMR) show the following composition:

| Sample | Lutensol ® AT 50 [wt %] | Anhydride [wt %] | Ester [wt %] | MAA [wt %] |
|---|---|---|---|---|
| after 6 h | 0 | 0.8 | 95.2 | 4.0 |
| after 1 h | 0 | 0 | 95.0 | 5.0 |
| after dilution with MAA | 0 | 0 | 44.8 | 54.2 |

Example 10

Reaction of Emulgin® BA 25 with Methacrylic Anhydride and Sodium Hydroxide as Catalyst To a 0.75 L flange flask fitted with an inclined blade stirrer (500 rpm) and also a condenser were added 837 g of Emulgin® BA 25 (0.6 mol, containing 0.22% water) as initial charge and melted at 85° C. bath temperature. While maintaining a pot temperature of 68° C., 380 mg of BHT (400 ppm), 88.5 g of methacrylic anhydride (0.54 mol, 94% strength, containing 2000 ppm of Topanol A) and also aqueous NaOH (50% strength, 0.96 g, 2 mol %) were added while passing air through the flask at 3.5 L/h. After 30 minutes, a further 19.7 g of methacrylic anhydride (0.12 mol) were added and the pot temperature was raised to 90-95° C.

After 6 h, the mixture was cooled down to 61° C. pot temperature and admixed with methanol (11.4 g). After 1 h, the mixture was removed while still warm.

The samples (TAI-NMR) show the following composition:

| Sample | Emulgin ® BA 25 [wt %] | Anhydride [wt %] | Ester [wt %] | MAA [wt %] | MeOH [wt %] |
|---|---|---|---|---|---|
| after 6 h | 0 | 0.4 | 93.1 | 6.5 | 0 |
| after 1 h quench | 0 | 0 | 92.9 | 6.6 | 0.5 |

Example 11

Reaction of Pluriol® A2010E with Methacrylic Anhydride and Sodium Hydroxide as Catalyst To a 1.6 L flange flask fitted with an anchor stirrer (220 rpm) and also a condenser were added 1000 g of Pluriol® A2010E (0.5 mol, contains 0.21% water) as initial charge and melted at 100° C. bath temperature. While maintaining a pot temperature of 94° C., 438 mg of BHT (400 ppm), 73.8 g of methacrylic anhydride (0.45 mol, 94% strength, containing 2000 ppm of Topanol A) and also aqueous NaOH (50%, 0.8 g, 1.5 mol %) were added while passing air through the flask at 3.5 L/h. After 30 minutes, a further 20.5 g of methacrylic anhydride (0.13 mol) were added. After 6 h, the mixture was cooled down to 68° C. pot temperature and admixed with methanol (10 g). After 30 min, 975 g of methacrylic acid were added to the mixture and the product was removed.

The samples (TAI-NMR) showed the following composition:

| Sample | Pluriol ® A2010E [wt %] | Anhydride [wt %] | Ester [wt %] | MAA [wt %] |
|---|---|---|---|---|
| after 6 h | 0 | 0.6 | 94.8 | 4.7 |
| after 30 min quench | 0 | 0 | 95.4 | 4.6 |

We claim:

1. A process for preparing a (meth)acrylic ester (E) of a polyalkoxy-containing alcohol, the process comprising reacting a polyalkoxy-containing alcohol (P) of formula (I)

$$R^1 \!\!-\!\!\left(\!\!\begin{array}{c}O\\|\\R^2\end{array}\!\!\right)_{\!\!m}\!\!\left(\!\!\begin{array}{c}R^3\\|\\O\end{array}\!\!\right)_{\!\!n}\!\!OH \quad (I)$$

wherein
$R^1$ is hydrogen, a hydroxyl group or a straight-chain or branched, saturated or unsaturated alcohol of 1 to 30 carbon atoms,
$R^2$ and $R^3$ are each independently H or methyl, and
m and n are each independently an integer between 0 and 100, with the proviso that m and n cannot both be 0, with a (meth)acrylic anhydride (A) in the presence of a basic catalyst (K) having a $pK_B$ value of not more than 7.0 and of a sterically hindered polymerization inhibitor, wherein the reaction mixture is quenched with a $C_1$-$C_6$ alkanol after the reaction has ended.

2. The process according to claim 1, wherein $R^2$ and $R^3$ are each hydrogen in formula (I).

3. The process according to claim 1, wherein m and n in formula (I) are each independently integers in the range from 5 to 90.

4. The process according to claim 3, wherein m and n in formula (I) are each independently integers in the range from 5 to 50.

5. The process according to claim 1, wherein the substituent $R^1$ is a straight-chain, saturated or unsaturated primary alcohol of 6 to 22 carbon atoms.

6. The process according to claim 1, wherein the basic catalyst (K) has a $pK_B$ value of not more than 3.0.

7. The process according to claim 6, wherein the basic catalyst is selected from the group consisting of alkali metal and alkaline earth metal hydroxides and inorganic salts.

8. The process according to claim 7, wherein the basic catalyst is lithium hydroxide, sodium hydroxide, potassium hydroxide, magnesium hydroxide or calcium hydroxide.

9. The process according to claim 7, wherein the inorganic salt comprises at least one anion selected from the group consisting of carbonate ($CO_3^{2-}$), bicarbonate ($HCO^{3-}$), phosphate ($PO_4^{3-}$), hydrogenphosphate ($HPO_4^{2-}$), dihydrogenphosphate ($H_2PO^{4-}$), sulfate ($SO_4^{2-}$), sulfite ($SO_3^{2-}$) and carboxylate ($R^4$—COO—), where $R^4$ is $C_1$-$C_{18}$ alkyl; $C_2$-$C_{18}$ alkyl optionally interrupted by an oxygen atom, a sulfur atom, a substituted or unsubstituted imino group, or any combination thereof; or $C_6$-$C_{14}$ aryl.

10. The process according to claim 9, wherein the inorganic salt is selected from the group consisting of $Li_3PO_4$, $K_3PO_4$, $Na_3PO_4$, $K_2CO_3$ and $Na_2CO_3$ and also hydrates thereof.

11. The process according to claim 1, wherein the amount of (meth)acrylic anhydride (A) is reacted at not more than 1.35 mol per mole of the polyalkoxy-containing alcohol (P).

12. The process according to claim 11, wherein the amount of (meth)acrylic anhydride (A) is reacted at not more than 1.15 mol per mole of the polyalkoxy-containing alcohol (P).

13. The process according to claim 1 wherein the sterically hindered polymerization inhibitor does not degrade during the course of the reaction.

14. The process according to claim 13, wherein the sterically hindered polymerization inhibitor is selected from the group consisting of 2,6-di-tert-butylphenol, 2,6-di-tert-butyl-4-methylphenol and phenothiazine.

15. The process according to claim 1, wherein the $C_1$-$C_6$ alkanol is selected from the group consisting of methanol, ethanol, propanol and isopropanol.

16. The process according to claim 15, wherein the $C_1$-$C_6$ alkanol is selected from the group consisting of methanol and ethanol.

17. The process according to claim 1, wherein the quench time is up to 2 h, but not less than 30 minutes.

18. The process according claim 1, wherein the $C_1$-$C_6$ alkanol is added to the reaction medium in amounts of up to 5 wt %, based on total reaction medium.

19. A method for producing a dispersion, comprising employing a (meth)acrylic ester (E) of a polyalkoxy-containing alcohol as a monomer or comonomer.

* * * * *